United States Patent [19]

Esanu

[11] Patent Number: 4,492,701
[45] Date of Patent: Jan. 8, 1985

[54] ISOPROPYLAMINO PYRIMIDINE DERIVATIVE ITS PREPARATION AND THERAPEUTIC COMPOSITIONS CONTAINING THE SAME

[75] Inventor: André Esanu, Paris, France

[73] Assignee: Societe de Conseils de Recherches et d'Applications Scientifiques, Paris, France

[21] Appl. No.: 427,924

[22] Filed: Sep. 29, 1982

[30] Foreign Application Priority Data

Oct. 16, 1981 [GB] United Kingdom ................ 8131201

[51] Int. Cl.³ .................. A61K 31/505; C07D 239/42
[52] U.S. Cl. ..................................... 424/251; 544/298
[58] Field of Search ......................... 544/298; 424/251

[56] References Cited

U.S. PATENT DOCUMENTS 3,984,414  10/1976  Esanu ................................. 424/251
4,073,895   2/1978  Esanu ................................. 424/251

OTHER PUBLICATIONS

Brown, *The Pyrimidines, Supplement I*, 1970, Wiley-Interscience, N.Y., pp. 294–295.

*Primary Examiner*—Glennon H. Hollrah
*Assistant Examiner*—James H. Turnipseed
*Attorney, Agent, or Firm*—Lucas & Just

[57] ABSTRACT

This invention relates to the 2-isopropylamino-pyrimidine-N-oxide of the formula:

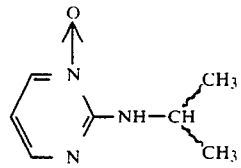

to a preparation process of the same consisting in submitting at 15° to 45° C., 2-isopropylamino pyrimidine to a smooth oxidation by stoichiometric proportions or a slight excess of up to 10% of an appropriate oxidizing agent and to a therapeutic composition of matter comprising said compound as an active ingredient therein.

7 Claims, No Drawings

ISOPROPYLAMINO PYRIMIDINE DERIVATIVE ITS PREPARATION AND THERAPEUTIC COMPOSITIONS CONTAINING THE SAME

The invention relates to an isopropylamine derivative to a process for its preparation and to therapeutic compositions containing the same.

The invention provides 2-isopropylamino-pyrimidine-N-oxide, which has the formula:

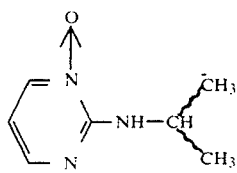

and therapeutically acceptable salts thereof.

This compound is particularly interesting in the field of nervous regeneration and for the treatment of muscular dystrophy.

According to the invention, 2-isopropylamino-pyrimidine-N-oxide may be prepared by smooth oxidation of 2-isopropylamino-pyrimidine by appropriate oxidising agents such as hydrogen peroxide, m-chloroperoxybenzoic acid, potassium peroxymonosulphate, chromic acid, perphosphoric acid, peracetic acid, sodium perborate or tertiobutyl hydroperoxide. The oxidising agent is used in stoichiemetric proportion or in a slight excess of up to 10% with respect to this proportion. The desired salts may be obtained by the usual techniques.

The invention is illustrated by the following example.

EXAMPLE

Into a 4 liter reactor fitted with stirring means and calcium chloride protection were poured 100 g (0.728 mol) of 2-isopropylamino-pyrimidine and 2 liters of acetone. After stirring, there was added 0.8 mol of m-chloroperoxybenzoic acid and the temperature was raised to about 35° C. Stirring was maintained for one hour after the addition and the mixture was then evaporated to dryness under reduced pressure. The residue was treated with 450 ml of water, which gives a precipitate, and with 245 ml (2.4 mol) of a soda wash saturated with sodium chloride. This solution was then treated with $CHCl_3$, which gives a new precipitate: after filtration, washing with diethyl ether and drying, there were obtained 99.2 g (yield 90%) of an oily product, elemental analysis of which showed it to correspond to the formula $C_7H_{11}ON_3$; the melting point of the base 74°–76° C. (Tottoli). This compound is highly soluble in water, methanol and has a good solubility in chloroform at room temperature. The pH of 5% water solution is 6.1–6.4.

The corresponding hydrochloride melts at 94° C. The succinate obtained by reaction of succinic acid on the base, in acetone at the boil, melts at 92° C.; maleate, aspartate and orthophosphate were also prepared by usual routes. However, as the base itself has a good water solubility, a good stability and favourable organoleptic characteristics, it can be used as such. The base is hereafter designated by "BN 1041".

TOXICITY

The toxicity was determined on female wistar rats I.P. and P.O. Values obtained by usual techniques were 1.2 g/kg for the first route and 1.9 g/kg for the second one.

PHARMACOLOGY

The experimentations performed have shown the interest of the compound of the invention on the growth and the regeneration of nerves; they have also evidenced a good analgesic activity, which is a highly interesting side effect.

(1) Compared action on the growing of neutritis

The action of the compound of the invention (BN 1041) was determined comparatively with this one of 2-isopropylamino pyrimidine orthophosphate (IAPP) on the growing of neuritis of spinal cord cells and terminal ramifications (rats) according to the method described in "La Nouvelle Presse Médicale", 11, No. 16-1238-1242. This in vitro experimentation was conducted on cultures of rats embryos (14 days) spinal cord cells, each 35 mm culture box containing half a spinal cord ($5.10^6$ cells).

Both compounds were tested at decreasing doses from $10^{-3}$ to $10^{-9} M$ in order to determine the toxicity limits, the concentrations leading to maximum and minimum action on neurone growth parameters and the results at three days for the optimum concentrations. The results are reported in the following table.

|  | IAPP | BN 1041 |
|---|---|---|
| Toxicity limit | $> 10_M{}^{-5}$ | $> 10_M{}^{-2}$ |
| Concentration at which growth appears despite the toxic action | $10_M{}^{-3}$ | $10_M{}^{-3}$ |
| Best operating concentration | $10_M{}^{-5}$ | $10_M{}^{-9}$ |

It is to be noticed that a growth appears at the same concentration of $10^{-3}{}_M$ which is more (IAPP) or less (BN 1041) toxic although the best concentrations are different: $10^{-5}{}_M$ for IAPP or $10^{-9}{}_M$ for the compound of the invention. In these concentrations, the reference compound is toxic but the compound of the invention is deprived of any toxicity.

(2) Reinnervation of Skeletal muscle (Rat)

This experimentation was conducted comparatively with 2-isopropylamino pyrimidine orthophosphate as reference compound on adult male albinos rats. Three batches of each 5 rats were used: one for control, one for reference compound and one for the compound of the invention.

On all the animals, a lesion of the left sciatic nerve was provoked by 3 or 4 local applications of a liquid nitrogen cryode (at about −180° C.) on the same region of the nerve, which results in a frozen zone of about 2–3 mm. This technique is more efficient, more reliable, more easily reproducible than the known technique of mechanical crushing of the nerve; moreover, the recovery is faster and more complete.

The day after the lesion, control batch animals were injected I.P. 1 ml/100 g of physiologic saline solution whereas the second batch animal received I.P. 300 mg/Kg of reference compound and the third batch animals, 100 mg/kg of the compound of the invention.

The progress of nerve regeneration is checked on the following days by electric stimulation of the nerve. The reinnervation is obtained at 16 days for batches 2 and 3 and at 18 days for control batch.

At 18 days the recovery is appreciated on the internal left gastrocnemic muscle by comparison with its right homologue, by the techniques of intracellular recording of motory plate potentials.

On the killed animals (at 18 days) sciatic nerves of rats treated, by the product of the invention show more than 37% of multiple innervation, by reference compound, 30%; control animals show only 16% multiple innervation. It is to be noticed that the product of the invention leads to a more regular reinnervation, involving frequently 2 to 3 axones by motory plate (reference compound 1-2 axone only).

(3) Analgesic activity oral administration of the various test compounds on the pain response to electrical stimulation of the dental pulp—i.e the analgesic activity—are summarised in Table 1. Approximate $ED_{50}$ values derived from the results of Table 1 are given in Table 2.

All three test compounds showed activity in this test. The data in Table 1 shows that galfenine reached peak activity by 30 minutes post-dose and activity was still present in one animal at 150 minutes after dosing. Compound IAPP showed peak activity by 90 minutes post-dose, with some effect still present at 300 minutes post-dose. A more active compound than either glafenine or IAPP appeared to be BN 1041, whose peak activity was reached 120 minutes after dosing and with residual effects up to 300 minutes; the $ED_{50}$ value at time of peak activity was approximately 30 mg/kg.

TABLE 1

| Treatment | Dose (mg/kg) p.o. | No. of monkeys showing analgesia at time (min) after dosing | | | | | | | | |
|---|---|---|---|---|---|---|---|---|---|---|
| | | 15 | 30 | 60 | 90 | 120 | 150 | 180 | 240 | 300 |
| Vehicle | — | 0/4 | 0/4 | 0/4 | 0/4 | 0/4 | 0/4 | 0/4 | 0/4 | 0/4 |
| Glafenine | 30 | 0/4 | ¼ | 0/4 | ¼ | ¼ | ¼ | ¼ | ¼ | ¼ |
| | 60 | ¼ | 2/4 | 2/4 | 2/4 | 2/4 | ¼ | 0/4 | 0/4 | 0/4 |
| IAPP | 30 | 0/4 | 0/4 | 0/4 | ¼ | 0/4 | ¼ | 0/4 | 0/4 | 0/4 |
| | 60 | 0/4 | 0/4 | ¼ | ¼ | ¼ | ¼ | ¼ | ¼ | ¼ |
| | 120 | ¼ | ¼ | ¼ | 2/4 | 2/4 | 2/4 | 2/4 | ¼ | ¼ |
| BN 1041 | 30 | ¼ | ¼ | ¼ | ¼ | 2/4 | 2/4 | ¼ | ¼ | ¼ |
| | 60 | ¼ | 2/4 | 2/4 | 2/4 | ¾ | ¾ | ¾ | ¾ | 2/4 |
| | 120 | 0/4 | 2/4 | 2/4 | 4/4 | 4/4 | 4/4 | ¾ | 2/4 | ¼ |

TABLE 2

| Treatment | Approximate $ED_{50}$ values (mg/kg) at time (min) post dose | | | | | | | | |
|---|---|---|---|---|---|---|---|---|---|
| | 15 | 30 | 60 | 90 | 120 | 150 | 180 | 240 | 300 |
| Glafenine | >60 | ~60 | ~60 | ~60 | ~60 | ~60 | >60 | >60 | >60 |
| IAPP | >120 | >120 | >120 | ~120 | ~120 | ~120 | ~120 | >120 | >120 |
| BN 1041 | >120 | ~85 | ~85 | 53 | ~30 | ~30 | 42 | ~42 | ? |

This activity has been determined by using the dental pulp stimulation test in the rhesus monkey. For comparison purposes, glafenine (30 and 60 mg/kg p.o.), 2-isopropylamino pyrimidine IAPP (30, 60 and 120 mg/kg p.o.) and the compound of the invention: BN 1041 (30, 60 and 120 mg/kg p.o.), have been tested for analgesic activity using inhibition of the pain response to stimulation of the dental pulp in the rhesus monkey (adult female rhesus monkeys Macaca mulatta).

The monkeys were trained to sit in individual restraining chairs. On the day of a test, prior to dosing, the electrode leads were connected to a Grass stimulator and the pain threshold for each animal was determined using a series of transient but increasing stimuli applied to the dental pulp. In each stimulation schedule the frequency, pulse width and duration of the stimulus remained constant at 10 Hz, 5 ms and 10 s respectively; only voltage was varied. The pain threshold was determined as the voltage required to produce individual reactions such as yawning and licking of the tooth. The animals were dosed orally and threshold voltages were applied 15, 30, 60, 90, 120, 150, 180, 240, and 300 minutes post-dose; the presence or absence of individual reactions to the threshold voltage were then noted.

An interval of at least seven days was allowed between each test.

Test compounds were administrated in aqueous 0.5% carboxymethyl-cellulose by oral gavage using a constant dose-volume of 4 ml/kg. Control animals received vehicle only at a dose volume of 4 ml/kg. The effects of The approximate $ED_{50}$ values were calculated using the method of moving averages (Thompson, W. R., Bacteriological Reviews, (1947), 11, 115–145).

PRESENTATION-POSOLOGY

This compound can be presented in any therapeutically acceptable form and, for instance, in tablets or in gelatine capsules containing 50 mg per dosage unit together with an excipient such as lactose; for injectable form the product may be dosed in phials containing at least 5 mg of active ingredient dissolved in water. As to the posology, oral administration requires from 100 mg to 1 g per diem whereas injectable form may be administered at doses between 5 mg to 100 mg per diem.

An example of the tablet form is given here under:

| | |
|---|---|
| 2-isopropylamino-pyrimidine-N—oxide | 50 mg |
| Microcrystalline cellulose | 20 mg |
| Corn starch | 15 mg |
| Talc | 7 mg |
| Silicic acid | 6 mg |
| Magnesium stearate | 2 mg |
| | 100 mg |

I claim:

1. 2-isopropylamino-pyrimidine-N-oxide of the formula:

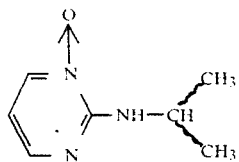

and therapeutically acceptable salt thereof.

2. A therapeutic composition for nervous regeneration comprising in a pharmaceutically acceptable carrier a compound according to claim 1 in an amount effective to induce nervous regeneration.

3. The therapeutic composition of claim 2 for oral administration wherein said compound is present in the amount from 100 mg. to 1 g.

4. The therapeutic composition of claim 2 in a form suitable for injection wherein said compound is present in the amount between 5 mg. to 100 gm.

5. A therapeutic composition for analgesic treatment comprising in a pharmaceutically acceptable carrier an analgesically effective amount of a compound according to claim 1.

6. The therapeutic composition of claim 5 for oral administration wherein said compound is present in the amount from 100 mg. to 1 g.

7. The therapeutic composition of claim 5 in a form suitable for injection wherein said compound is present in the amount between 5 mg. to 100 mg.

* * * * *

UNITED STATES PATENT AND TRADEMARK OFFICE
CERTIFICATE OF CORRECTION

PATENT NO. : 4,492,701
DATED : January 8, 1985
INVENTOR(S) : Andre Esanu

It is certified that error appears in the above-identified patent and that said Letters Patent are hereby corrected as shown below:

Column 2, lines 30-38, the data in the columns headed "IAPP" and "BN 1041", respectively, should appear as follows:

| IAPP | BN 1041 |
|---|---|
| $>10^{-5}M$ | $>10^{-2}M$ |
| $10^{-3}M$ | $10^{-3}M$ |
| $10^{-5}M$ | $10^{-9}M$ |

Column 2, line 11, change "neutritis" to --neuritis--.

Column 6, line 6, change "100 gm" to --100 mg--.

Signed and Sealed this

Eighteenth Day of June 1985

[SEAL]

Attest:

DONALD J. QUIGG

Attesting Officer     Acting Commissioner of Patents and Trademarks

UNITED STATES PATENT AND TRADEMARK OFFICE
CERTIFICATE OF CORRECTION

PATENT NO. : 4,492,701
DATED : January 8, 1985
INVENTOR(S) : Andre Esanu

It is certified that error appears in the above-identified patent and that said Letters Patent are hereby corrected as shown below:

Column 4, Table I should appear as follows:

| Treatment | Dose (mg/kg) p.o. | No. of monkeys showing analgesia at time (min) after dosing | | | | | | | | |
|---|---|---|---|---|---|---|---|---|---|---|
| | | 15 | 30 | 60 | 90 | 120 | 150 | 180 | 240 | 300 |
| Vehicle | - | 0/4 | 0/4 | 0/4 | 0/4 | 0/4 | 0/4 | 0/4 | 0/4 | 0/4 |
| Glafenine | 30 | 0/4 | 1/4 | 0/4 | 1/4 | 1/4 | 1/4 | 1/4 | 1/4 | 1/4 |
| | 60 | 1/4 | 2/4 | 2/4 | 2/4 | 2/4 | 1/4 | 0/4 | 0/4 | 0/4 |
| IAPP | 30 | 0/4 | 0/4 | 0/4 | 1/4 | 0/4 | 1/4 | 0/4 | 0/4 | 0/4 |
| | 60 | 0/4 | 0/4 | 1/4 | 1/4 | 1/4 | 1/4 | 1/4 | 1/4 | 1/4 |
| | 120 | 1/4 | 1/4 | 1/4 | 2/4 | 2/4 | 2/4 | 2/4 | 1/4 | 1/4 |
| BN 1041 | 30 | 1/4 | 1/4 | 1/4 | 1/4 | 2/4 | 2/4 | 1/4 | 1/4 | 1/4 |
| | 60 | 1/4 | 2/4 | 2/4 | 2/4 | 3/4 | 3/4 | 3/4 | 3/4 | 2/4 |
| | 120 | 0/4 | 2/4 | 2/4 | 4/4 | 4/4 | 4/4 | 3/4 | 2/4 | 1/4 |